US010365205B1

(12) United States Patent
Wu et al.

(10) Patent No.: US 10,365,205 B1
(45) Date of Patent: Jul. 30, 2019

(54) WATER QUALITY SENSOR

(71) Applicant: SOLTEAM OPTO, INC., Taoyuan (TW)

(72) Inventors: Chun-Yen Wu, Taoyuan (TW); Fu-Min Liang, Taoyuan (TW); Cheng-Ting Wu, Taoyuan (TW); Chia-Hao Chang, Taoyuan (TW); Chin-Feng Chen, Taoyuan (TW)

(73) Assignee: SOLTEAM OPTO, INC., Taoyuan (TW)

( * ) Notice: Subject to any disclaimer, the term of this patent is extended or adjusted under 35 U.S.C. 154(b) by 14 days.

(21) Appl. No.: 15/864,571

(22) Filed: Jan. 8, 2018

(51) Int. Cl.
*G01B 11/00* (2006.01)
*G01N 21/00* (2006.01)
*G01N 21/15* (2006.01)
*G01N 21/59* (2006.01)
*G01N 21/49* (2006.01)

(52) U.S. Cl.
CPC ............ *G01N 21/15* (2013.01); *G01N 21/49* (2013.01); *G01N 21/59* (2013.01); *G01N 2201/022* (2013.01)

(58) Field of Classification Search
CPC ........ G01N 21/15; G01N 21/49; G01N 21/59; G01N 21/534; G01N 21/85; G01N 2201/022; D06F 35/006; D06F 2202/02; A47L 15/4297

USPC .......................................... 356/394–401, 441
See application file for complete search history.

(56) References Cited

U.S. PATENT DOCUMENTS

| | | | | |
|---|---|---|---|---|
| 9,671,338 B1 * | 6/2017 | Wu | ...................... | G01N 21/49 |
| 10,130,238 B2 * | 11/2018 | Durham | .............. | A47L 15/0031 |
| 2016/0069830 A1 * | 3/2016 | Wu | ..................... | G01N 33/1886 73/61.61 |
| 2017/0234848 A1 * | 8/2017 | Cheng | .................... | G01N 21/17 73/61.41 |

* cited by examiner

*Primary Examiner* — Sunghee Y Gray
(74) *Attorney, Agent, or Firm* — Muncy, Geissler, Olds & Lowe, P.C.

(57) ABSTRACT

A water quality sensor includes a housing including a light transmissive bucket mounted in an electrical washing appliance and a light transmissive inner barrel mounted in the bucket, an actuation module mounted in the inner barrel for detecting a water quality of a washing solution in the electrical washing appliance. Thus, if the bucket is cracked during manufacturing or due to a collision, the contact actuation module can still be well protected by the inner barrel, so that the washing solution in the electrical washing machine does not directly flow into contact with the actuation module to cause an accidental short circuit of the circuit substrate of the actuation module, improving the water resistance and service life of the water quality sensor.

11 Claims, 5 Drawing Sheets

WATER QUALITY SENSOR

BACKGROUND OF THE INVENTION

1. Field of the Invention

The present invention relates to water quality sensor technology and more particularly, to a water quality sensor for use in an electrical washing appliance, which uses an inner barrel in a bucket for accommodating an actuation module to provide enhanced waterproof effect, preventing a short circuit of the actuation module.

2. Description of the Related Art

Many household appliances such as washing machines, dishwashers, and the like are designed for use with water and a washing solution or detergent to achieve cleaning. Thus, we can use these household appliances to wash clothes, dishes, kitchen utensils etc., instead of hand washing. When washing some objects in an electrical washing appliance, dust, fines, debris and other impurities in the objects and the applied washing solution or detergent can cause an increase in the turbidity of the applied water. Thus, the cleaning operation must be repeated several times until the objects to be cleaned are well cleaned so that the ion concentration in the cleaning water can be in line with test standards. Most electric washing machines and dishwashers are equipped with a water quality sensor to detect the particle concentration (undissolved detergent, impurities or dust or hair or clothing debris, cotton wool, etc.) in the applied water by means of emitting a light source and receiving a reflective light from the applied water so that the control system of the washing machine or dishwasher can determine the cleaning mode (for example, increasing the number of runs of the cleaning process or extending the cleaning time) according to the detected turbidity.

However, the housing of a water quality sensor can get cracked due to improper manufacturing or a collision during transportation. If coins, pebbles or other large particles exist in the cleaning water during a washing operation of an electrical washing appliance, these solid matters can hit the housing of the water quality sensor, causing the housing to get cracked. At this time, cleaning water can flow through the cracked area into the inside of the water quality sensor, causing a short circuit of the internal circuit board of the water quality sensor and leading to electrical washing appliance damage.

Therefore, it is desirable to provide a water quality sensor that eliminates the drawbacks and problems of the aforesaid prior art water quality sensor designs.

SUMMARY OF THE INVENTION

The present invention has been accomplished under the circumstances in view. It is therefore the main object of the present invention to provide a water quality sensor, which comprises a housing comprising a light transmissive bucket mounted in an electrical washing appliance and a light transmissive inner barrel mounted in the bucket, and an actuation module mounted in the inner barrel for detecting a water quality of a washing solution in the electrical washing appliance. Thus, if the bucket is cracked during manufacturing or due to a collision, the actuation module can still be well protected by the inner barrel, so that the washing solution in the electrical washing machine does not directly flow into contact with the actuation module to cause an accidental short circuit of the circuit substrate of the actuation module, improving the water resistance and service life of the water quality sensor.

Preferably, the housing further comprises a gasket ring. The gasket ring is made up of an elastic material and attached onto the inner barrel. After installation of the inner barrel in the bucket, the gasket ring is squeezed in between an outer flange of the inner barrel and an annular stop edge of the bucket and elastically deformed to seal the gap between the bucket and the inner barrel, providing a waterproof effect. Since the gasket ring is mounted around the outer perimeter of the inner barrel, an enclosed gap is defined between the bucket and the inner barrel. During transportation of the water quality sensor, the elastic prestress of the gasket ring and the design of the enclosed gap between the bucket and the inner barrel reduce vibrations and avoid impact between the bucket and inner barrel, achieving the purpose of enhancing the waterproof performance.

Preferably, the actuation module further comprises a light sensor consisting of a light-emitting component and a light-receiving component, and a light-shading member. The light-emitting component of the light sensor is inserted in a through hole of a light-shading member. The light-shading member comprises a barrier layer disposed between the light-emitting component and the light-receiving component. When the light-emitting component is activated to emit light, the light emitted by the light-emitting component can simply go toward the outside of the inner barrel and is prohibited from directly passing to the light-receiving component, avoiding saturation of the light-receiving component and generation of crosstalk noises before reaching of the emitted light to the washing solution in the electrical washing appliance.

Preferably, the inner barrel of the housing further comprises condenser means. The condenser means comprises a condensing cone located on a top surface of the light transmissive bottom wall of the inner barrel. The light condensing performance of the condensing cone of the condenser means enhances the sensing consistency and accuracy of the light-receiving component, improving the determination accuracy of the light-receiving component and water utilization of the electrical washing appliance.

Other advantages and features of the present invention will be fully understood by reference to the following specification in conjunction with the accompanying drawings, in which like reference signs denote like components of structure.

DETAILED DESCRIPTION OF THE PREFERRED EMBODIMENT

Figure 1:
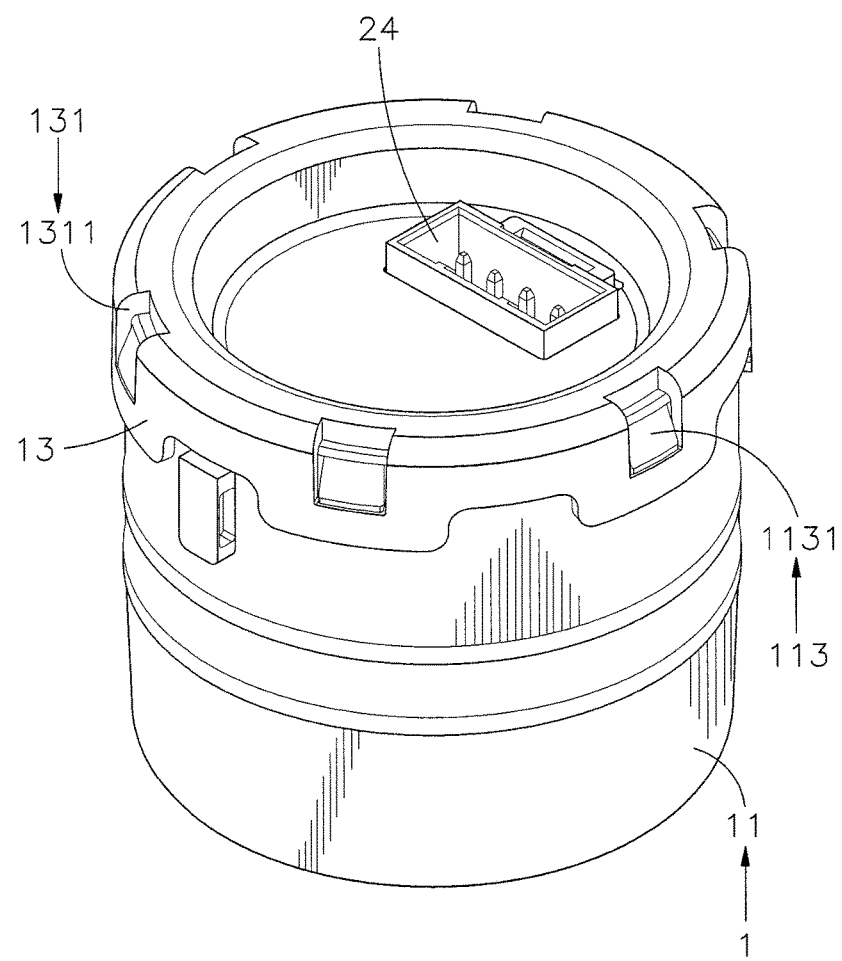
FIG. 1 is an oblique top elevational view of a water quality sensor in accordance with a first embodiment of the present invention.
Figure 2:
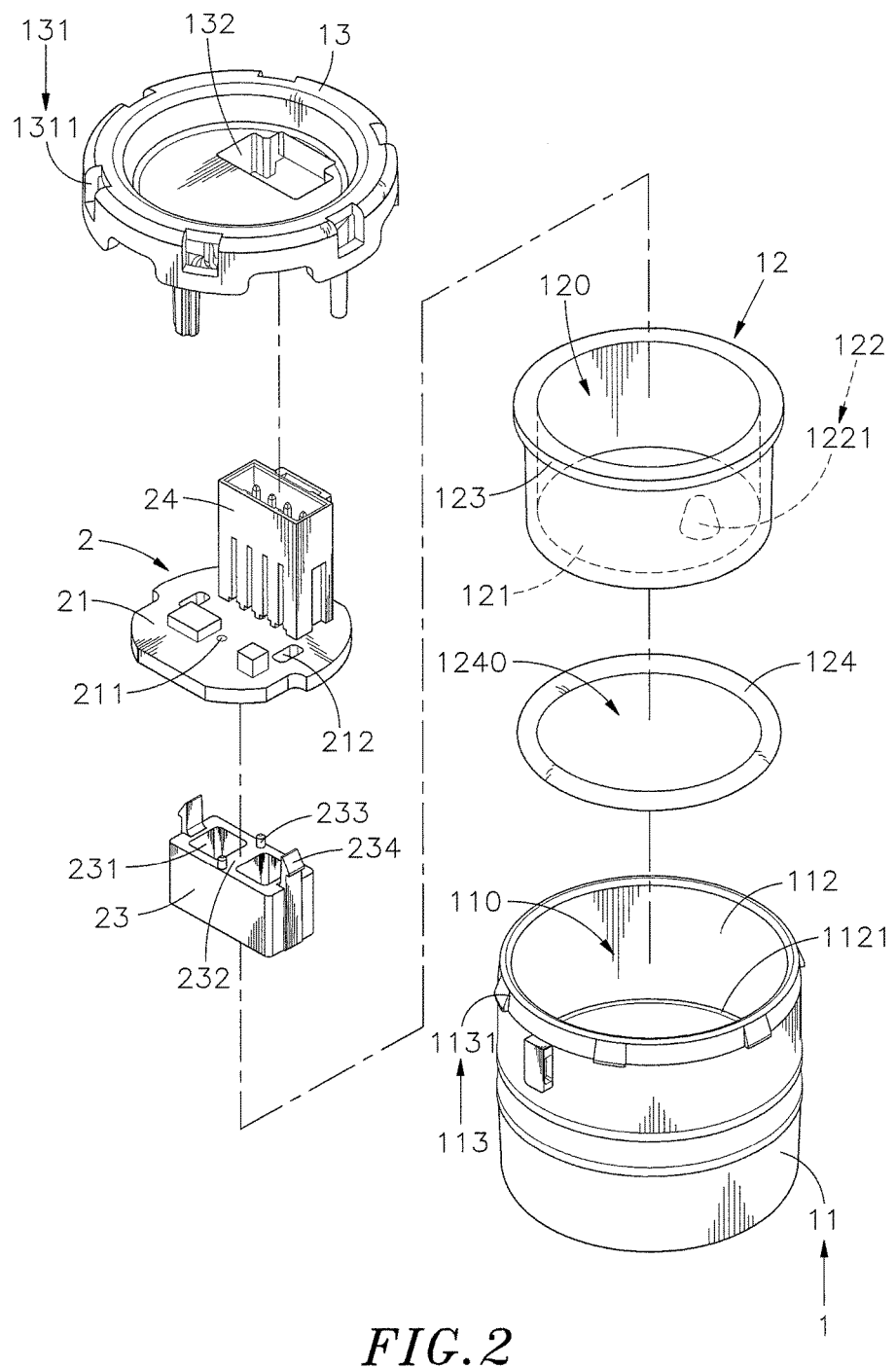
FIG. 2 is an exploded view of the water quality sensor in accordance with the first embodiment of the present invention.
Figure 3:
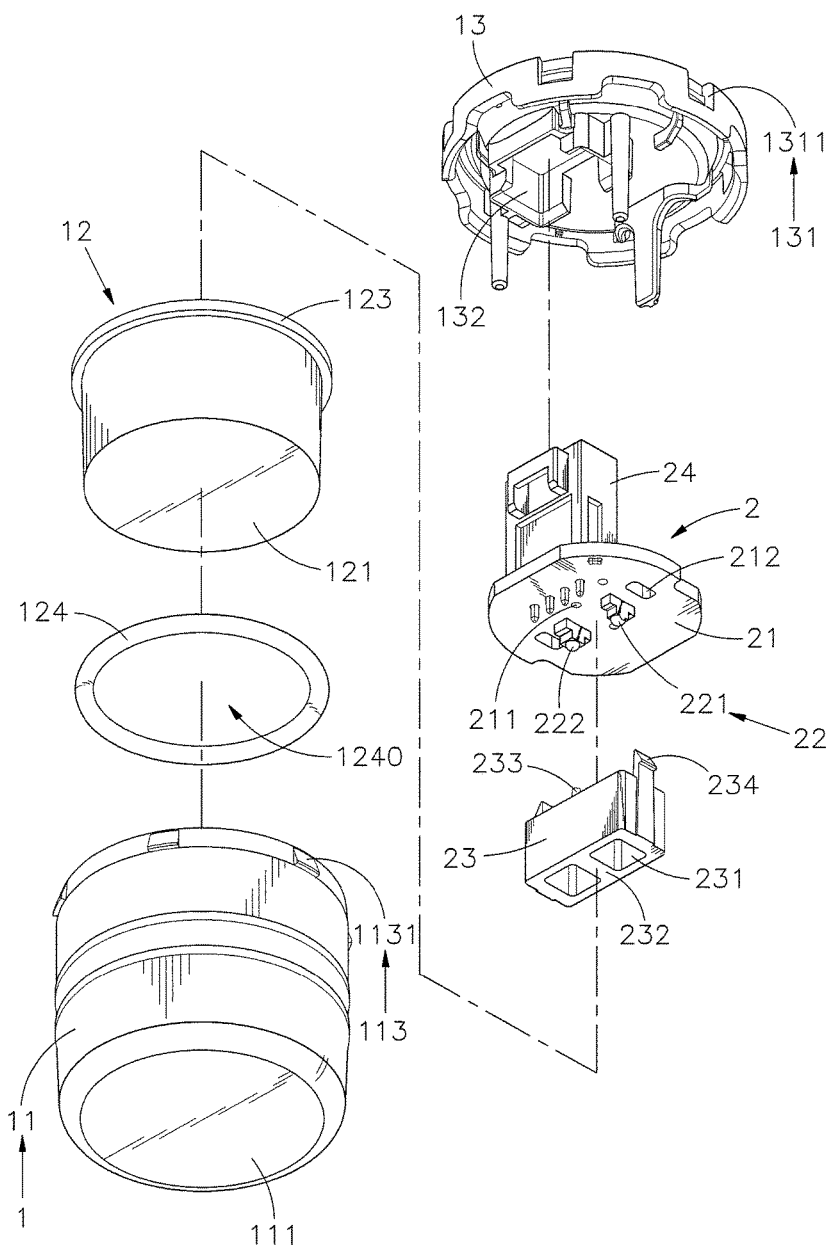
FIG. 3 corresponds to FIG. 2 when viewed from another angle.
Figure 4:
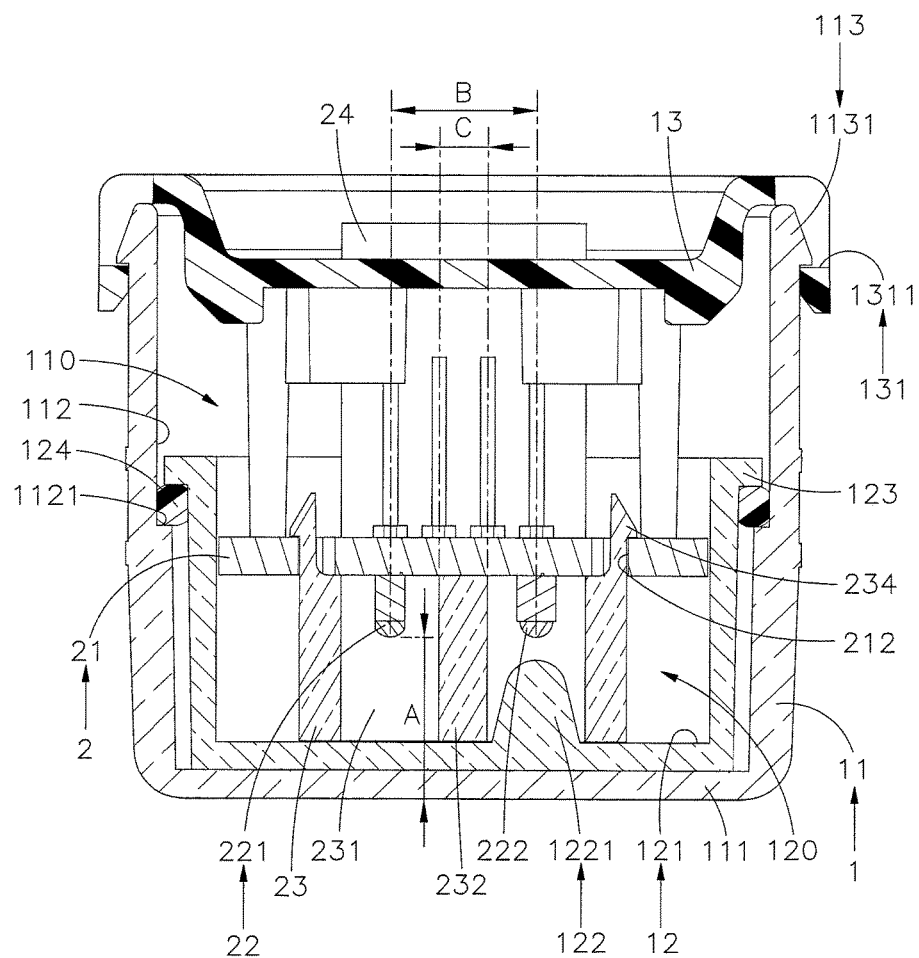
FIG. 4 is a sectional side view of the water quality sensor in accordance with the first embodiment of the present invention.
Figure 5:
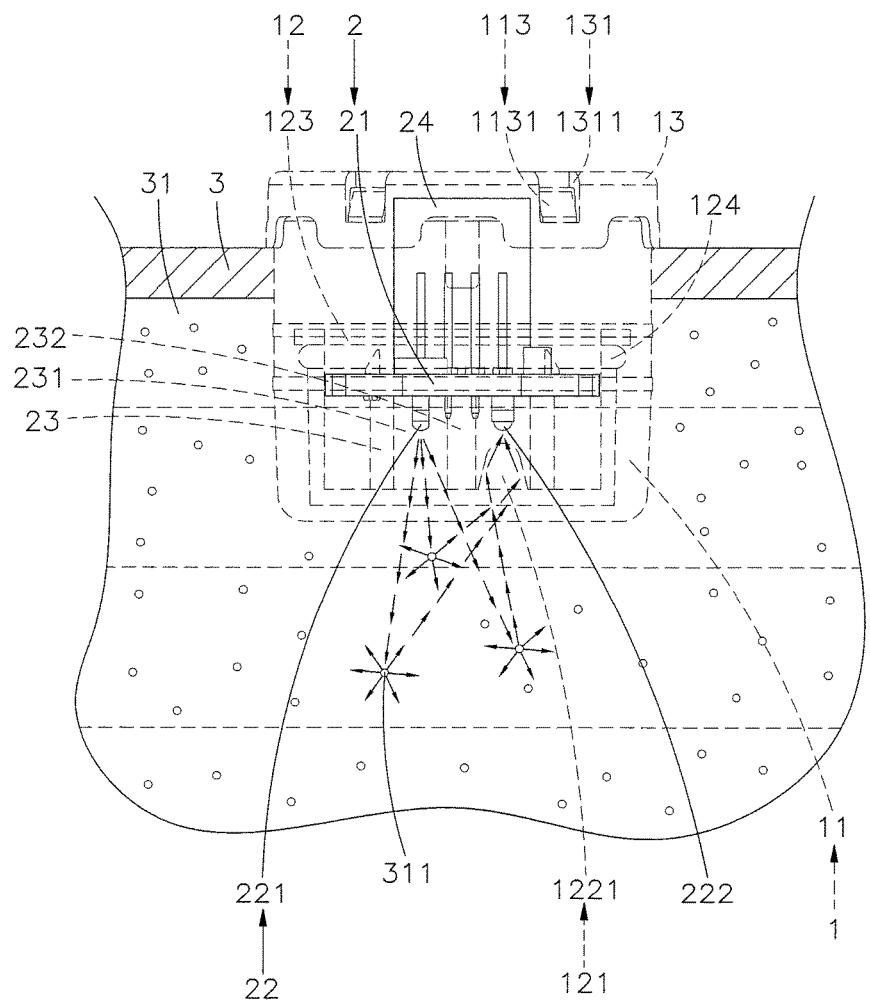
FIG. 5 is a schematic applied view of the present invention, illustrating the water quality sensor used in an electrical washing appliance.

Referring to FIGS. 1-5, a water quality sensor in accordance with a first embodiment of the present invention is shown. The water quality sensor comprises a housing 1 and an actuation module 2.

The housing 1 comprises a bucket 11, an inner barrel 12 and a cover 13. The bucket 11 comprises a transparent panel 111, an accommodation chamber 110 defined therein above the transparent panel 111, an expanded top open space 112 disposed in communication with a top side of the accommodation chamber 110, an annular stop edge 1121 defined therein between the expanded top open space 112 and the accommodation chamber 110, and a male engagement structure 113 that comprises a plurality of hook blocks 1131 equiangularly spaced around the periphery of a top side of the bucket 11. The inner barrel 12 is made up of a transparent material and accommodated in the accommodation chamber 10 of the bucket 11, comprising a light transmissive bottom wall 121, an inner receiving chamber 120 defined therein at a top side of the light transmissive bottom wall 121, condenser means 122 located at the light transmissive bottom wall 121, the condenser means 122 comprises a condensing cone 1221. The housing 1 further comprises a gasket ring 124 attached onto the inner barrel 12 and stopped between an outer flange 123 and the annular stop edge 1121. The gasket ring 124 defines therein a ring hole 1240 for the insertion of the inner barrel 12. The cover 13 is capped on the top side of the bucket 11, comprising a center through hole 132 cut through opposing top and bottom surface thereof, and a female engagement structure 131 that comprises a plurality of hook holes 1311 respectively forced into engagement with the hook blocks 1131 of the male engagement structure 113 of the cover 13.

The actuation module 2 comprises a circuit substrate 21, a light sensor 22, a light-shading member 23 and an electrical connector 24. The circuit substrate 21 is horizontally positioned in the inner receiving chamber 120 of the inner barrel 12 and disposed in parallel to the light transmissive bottom wall 121, a plurality of position-limiting holes 211 and a plurality of retaining holes 212 cut through the circuit substrate 21. The light sensor 22 comprises a light-emitting component 221 and a light-receiving component 222 respectively mounted on a bottom surface of the circuit substrate 21 and kept apart from the light transmissive bottom wall 121 of the inner barrel 12 at a predetermined distance. Further, the light-emitting component 221 and the light-receiving component 222 are spaced from each other at a predetermined distance. Further, the light-receiving component 222 is spaced from the condensing cone 1221 of the condenser means 122 at a predetermined distance. The light-shading member 23 disposed below the light-emitting component 221, comprising a through hole 231 cut through opposing top and bottom surfaces thereof for the insertion of the light-emitting component 221, a barrier layer 232 disposed between the light-emitting component 221 and the light-receiving component 222, a plurality of pins 233 spaced around the through hole 231 and plugged into respective position-limiting holes 211 and a plurality of retaining arms 234 respectively fastened to the retaining holes 212. The electrical connector 24 electrically mounted in an opposing top surface of the circuit substrate 21 and positioned in the center through hole 132 of the cover 13.

In this embodiment, the bucket 11 of the housing 1 comprises the transparent panel 111 at the bottom side of the accommodation chamber 110 for the passing of light. Alternatively, the bucket 11 can adopt a transparent design for the passing of light in any angle. Further, the gasket ring 124 of the inner barrel 12 is made up of an elastic material, for example, silicon rubber or rubber.

Further, the light-emitting component 221 and light-receiving component 222 of the light sensor 22 are mounted to the bottom surface of the circuit substrate 21 using surface mount technology or dual inline package. Further, the light-emitting component 221 of the light sensor 22 can be an infrared light emitter, UV light emitter or laser light emitter; the light-receiving component 222 can be digital type of ambient light sensor, or a light sensor of wavelength corresponding to the wavelength of the light-emitting component 221. Further, the distance A between the light sensor 22 of the actuation module 2 and the outer surface of the transparent panel 111 of the bucket 11 is within 1.5~15 mm. Further, the light-emitting component 221 and light-receiving component 222 of the light sensor 22 are electrically connected to the circuit substrate 21; the distance B between the light-emitting component 221 and the light-receiving component 222 is within 3~10 mm; the thickness C of the barrier layer 232 of the light-shading member 23 between the light-emitting component 221 and the light-receiving component 222 is within 1~5 mm.

Further, in this embodiment, the light-shading member 23 of the actuation module 2 is disposed at the bottom side of the light-emitting component 221 of the light sensor 22, and the through hole 231 of the light-shading member 23 is configured to face toward the light-emitting component 221. However, in actual application, the light-shading member 23 can be configured to surround the light sensor 22, providing two through holes 231 corresponding to the light-emitting component 221 and the light-receiving component 222 respectively.

In application, the water quality sensor is installed in an electrical washing appliance 3 (such as washing machine or dishwasher) to face the transparent panel 111 of the bucket 11 toward the inside of the washing chamber of the electrical washing appliance 3, and then electrically connect the electrical connector 24 of the actuation module 2 to an external power source for enabling the actuation module 2 to obtain the necessary working power supply. When the electrical washing appliance 3 starts up the washing process, the circuit substrate 21 of the actuation module 2 drives the light-emitting component 221 of the light sensor 22 to emit light out of the through hole 231 of the light-shading member 23 through the light transmissive bottom wall 121 of the inner barrel 12 and the transparent panel 111 of the bucket 11 toward a washing solution 31 in the electrical washing appliance 3. Under normal conditions, the reflection of light in the washing solution 31 is rather weak. On the contrary, if many particles 311 (such as soil, sand or washing powder) are presented in the washing solution 31, the emitted light collides with the particles 311 in the washing solution 31 and scatters. At this time, a part of light in the washing solution 31 enters the inner barrel 12, and the condensing cone 1221 of the condenser means 122 of the inner barrel 12 condenses the incident light onto the light-receiving component 222 of the light sensor 22 for detection, obtaining a digital sensing value (for example, turbidity value or photometric value) from the washing solution 31. Thus, according to the detected digital sensing value, the electrical washing appliance 3 can determine whether the number of particles 311 in the washing solution 31 surpasses a predetermined value, and then decide if to continue the washing process.

Further, the actuation module 2 is accommodated in the inner receiving chamber 120 of the inner barrel 12; the inner barrel 12 is accommodated in the bucket 11. Thus, if the bucket 11 is cracked during manufacturing or due to a collision, the actuation module 2 can still be well protected by the inner barrel 12 in the bucket 11, so that the washing solution 31 in the electrical washing machine 3 does not directly flow into contact with the actuation module 2 to cause an accidental short circuit of the circuit substrate 21 of the actuation module 2, improving the water resistance and service life of the water quality sensor.

Further, the gasket ring 124 that is attached onto the inner barrel 12 is made up of an elastic material. After installation of the inner barrel 12 in the accommodation chamber 110 of the bucket 11, the gasket ring 124 is squeezed in between the outer flange 123 and the annular stop edge 1121 of expanded top open space 112 and elastically deformed to seal the gap between the bucket 11 and the inner barrel 12, providing a waterproof effect. Since the gasket ring 124 is mounted around the outer perimeter of the inner barrel 12, an enclosed gap is defined between the bucket 11 and the inner barrel 12. During transportation of the water quality sensor, the elastic prestress of the gasket ring 124 and the design of the enclosed gap between the bucket 11 and the inner barrel 12 reduce vibrations and avoid impact between the bucket 11 and inner barrel 12, achieving the purpose of enhancing the waterproof performance.

Further, the light-shading member 23 is disposed at the bottom side of the light-emitting component 221 of the light sensor 22 and the light-emitting component 221 is inserted into the through hole 231 of the light-shading member 23. Further, the barrier layer 232 of the light-shading member 23 is disposed between the light-emitting component 221 and the light-receiving component 222. When the light-emitting component 221 is activated to emit light, the light emitted by the light-emitting component 221 can simply go toward the outside of the inner barrel 12 and is prohibited from directly passing to the light-receiving component 222, avoiding saturation of the light-receiving component 222 and generation of crosstalk noises before reaching of the emitted light to the washing solution 31 in the electrical washing appliance 3. Further, the light condensing performance of the condensing cone 1221 of the condenser means 122 enhances the sensing consistency and accuracy of the light-receiving component 222, improving the determination accuracy of the light-receiving component 222 and water utilization of the electrical washing appliance 3.

Although a particular embodiment of the invention has been described in detail for purposes of illustration, various modifications and enhancements may be made without departing from the spirit and scope of the invention. Accordingly, the invention is not to be limited except as by the appended claims.

What the invention claimed is:

1. A water quality sensor, comprising:
a housing comprising a bucket, an inner barrel mounted in said bucket and a cover capped on said bucket, said bucket comprising a transparent panel, an accommodation chamber defined therein above said transparent panel for accommodating said inner barrel and a male engagement structure provided at a top side thereof, said inner barrel comprising a light transmissive bottom wall facing toward said transparent panel of said bucket and an inner receiving chamber defined therein above said light transmissive bottom wall, said cover comprising a female engagement structure arranged around the periphery thereof and forced into engagement with said male engagement structure; and
an actuation module comprising a circuit substrate horizontally mounted in said inner receiving chamber of said inner barrel and disposed in parallel to said transparent bottom wall, a light sensor mounted on a bottom surface of said circuit substrate and electrically connected to said circuit substrate and an electrical connector electrically mounted in an opposing top surface of said circuit substrate, said light sensor comprising a light-emitting component and a light-receiving component spaced from each other at a predetermined distance and a light-shading member disposed at a bottom side of said light-emitting component, said light-shading member comprising a through hole for the insertion of said light-emitting component and a barrier layer disposed between said light-emitting component and said light-receiving component.

2. The water quality sensor as claimed in claim 1, wherein said bucket further comprises an expanded top open space in communication with a top side of said accommodation chamber, and an annular stop edge defined therein between said expanded top open space and said accommodation chamber.

3. The water quality sensor as claimed in claim 2, wherein an inner barrel further comprises an outer flange extended around an inner receiving chamber, a gasket ring made up of an elastic material and mounted around the periphery thereof and stopped between said outer flange of said annular stop edge of said bucket, said gasket ring defining therein a ring hole for the insertion of said inner barrel.

4. The water quality sensor as claimed in claim 1, wherein said male engagement structure of said bucket comprises a plurality of hook blocks spaced around the periphery of said bucket; said female engagement structure of said cover comprises a plurality of hook holes respectively forced into engagement with said hook blocks of said male engagement structure of said bucket; said cover further comprises a center through hole for the positioning of said electrical connector.

5. The water quality sensor as claimed in claim 1, wherein said inner barrel of said housing is made up of a transparent material.

6. The water quality sensor as claimed in claim 1, wherein said inner barrel further comprises condenser means located on a top surface of said light transmissive bottom wall and spaced from said light-receiving component at a predetermined distance, said condenser means comprises a condensing cone facing toward said light-receiving component.

7. The water quality sensor as claimed in claim 1, wherein said circuit substrate of said actuation module comprises a plurality of position-limiting holes and a plurality of retaining holes cut through opposing top and bottom surfaces thereof; said light-shading member comprises a plurality of pins spaced around the through hole thereof and respectively plugged into the respective said position-limiting holes and a plurality of retaining arms respectively fastened to the respective said retaining holes.

8. The water quality sensor as claimed in claim 1, wherein said light-emitting component of said light sensor is selectively an infrared light emitter, UV light emitter or laser light emitter; said light-receiving component of said light sensor is selectively a digital type of ambient light sensor or a light sensor of wavelength corresponding to the wavelength of said light-emitting component;

said light-emitting component and said light-receiving component are selectively mounted to said circuit substrate by surface mount technology or dual inline package.

9. The water quality sensor as claimed in claim 1, wherein the distance between the center of said light-emitting component and the center of said light-receiving component is within 3~10 mm.

10. The water quality sensor as claimed in claim 1, wherein the distance between said light sensor of said actuation module and the outer surface of said transparent panel of said bucket is within 1.5~15 mm.

11. The water quality sensor as claimed in claim 1, wherein the thickness of said barrier layer of said light-shading member between said light-emitting component and said light-receiving component is within 1~5 mm.

* * * * *